US011203556B2

(12) United States Patent
Uehara et al.

(10) Patent No.: US 11,203,556 B2
(45) Date of Patent: Dec. 21, 2021

(54) DIMERIZATION OF CYCLOPENTADIENE USING REACTIVE JET MIXING

(71) Applicant: SABIC Global Technologies B.V., Bergen op Zoom (NL)

(72) Inventors: Ernesto Uehara, Riyadh (SA); Mohammed Sabri Abdel Ghani, Riyadh (SA); Retheesh Madhusudanan Vanchiyil, Bangalore (IN); Ananth Sharma, Bangalore (IN); John Byron Smith Rajarethnam, Bangalore (IN)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 17/058,974

(22) PCT Filed: May 13, 2019

(86) PCT No.: PCT/IB2019/053953
§ 371 (c)(1),
(2) Date: Nov. 25, 2020

(87) PCT Pub. No.: WO2019/234524
PCT Pub. Date: Dec. 12, 2019

(65) Prior Publication Data
US 2021/0221754 A1 Jul. 22, 2021

Related U.S. Application Data

(60) Provisional application No. 62/680,211, filed on Jun. 4, 2018.

(51) Int. Cl.
*C07C 2/50* (2006.01)
*B01F 5/02* (2006.01)
*C07C 13/61* (2006.01)

(52) U.S. Cl.
CPC .............. *C07C 2/50* (2013.01); *B01F 5/0256* (2013.01); *C07C 13/61* (2013.01); *C07C 2603/68* (2017.05)

(58) Field of Classification Search
CPC .... C07C 2/02; C07C 2/04; C07C 2/50; C07C 2603/68; C07C 13/61; B01F 5/0256
See application file for complete search history.

(56) References Cited

U.S. PATENT DOCUMENTS

| 2,813,135 A | 11/1957 | Johnson et al. |
| 3,196,188 A | 7/1965 | Parrish et al. |

(Continued)

FOREIGN PATENT DOCUMENTS

| CN | 1160035 A | 9/1997 |
| GB | 1187898 A | 4/1970 |
| WO | WO0236529 A1 | 5/2002 |

OTHER PUBLICATIONS

International Search Report and Written Opinion for PCT/IB2019/053953 dated Sep. 3, 2019, 9 pages.

*Primary Examiner* — Youngsul Jeong
*Assistant Examiner* — Jason Y Chong
(74) *Attorney, Agent, or Firm* — Norton Rose Fulbright US LLP

(57) ABSTRACT

Systems and methods for producing dicyclopentadiene from cyclopentadiene using reactive jet mixing are disclosed. A $C_5$ hydrocarbon mixture that comprises cyclopentadiene ($C_5H_6$) is injected as a jet stream into $C_5$ hydrocarbon liquid in a reactor tank. Under appropriate reaction conditions, cyclopentadiene is dimerized to form dicyclopentadiene.

17 Claims, 4 Drawing Sheets

(56) References Cited

U.S. PATENT DOCUMENTS

| | | | |
|---|---|---|---|
| 3,700,741 A | 10/1972 | Aubry et al. | |
| 6,093,789 A * | 7/2000 | Schubart | C11D 3/3719 528/328 |
| 2006/0111586 A1 | 5/2006 | Schladenhauffen et al. | |

* cited by examiner

DIMERIZATION OF CYCLOPENTADIENE USING REACTIVE JET MIXING

CROSS REFERENCE TO RELATED APPLICATIONS

This application is a national phase application under 35 U.S.C. § 371 of International Application No. PCT/IB2019/053953 filed May 13, 2019, which claims priority to U.S. Provisional Patent Application No. 62/680,211 filed Jun. 4, 2018. The entire contents of each of the above-referenced disclosures is specifically incorporated by reference herein without disclaimer.

FIELD OF INVENTION

The present invention generally relates to dimerization of cyclopentadiene. More specifically, the present invention relates to systems and methods for dimerizing cyclopentadiene to dicyclopentadiene using jet mixing.

BACKGROUND OF THE INVENTION

Dicyclopentadiene is used as a highly reactive intermediate for producing resins such as unsaturated polyesters and aromatic hydrocarbons. Generally, dicyclopentadiene is formed by dimerization of cyclopentadiene, which is a component of pygas generated from steam cracking of naphtha. In a conventional process of cyclopentadiene dimerization, a tubular reactor is used to provide a relatively long residence time that is sufficient to achieve a high conversion rate. The tubular reactor is typically surrounded by a large heat sink medium because the cyclopentadiene dimerization is highly exothermic. However, the long residence time can only be achieved with very long tubular reactor. Another instance is to use a large tank with one or more impellers to quickly mix the liquid and dissipate the heat generated during the dimerization reaction.

However, the economic feasibility of the conventional cyclopentadiene dimerization process is relatively limited. First of all, for the conventional method to achieve a cyclopentadiene conversion rate of above 50%, the energy demand is relatively high as the reactor has to be kept at an elevated reaction temperature for an extended period to achieve the required long residence time. Additionally, impellers in the tank reactors also demand a lot of energy. Thus, overall, the energy consumption of the conventional dimerization method is high. Moreover, impellers cannot sufficiently mix the liquid in the reactor, and such mixing forms hot spots in the liquid in the cyclopentadiene dimerization reactor. These hot spots not only limit the conversion rate of cyclopentadiene, but also induce side reactions for cyclopentadiene to form higher polymers other than dimers. Therefore, improvements in this field are desired.

BRIEF SUMMARY OF THE INVENTION

A method has been discovered for dimerizing cyclopentadiene to form dicyclopentadiene. By using a jet mixer to inject a $C_5$ hydrocarbon mixture comprising cyclopentadiene into a $C_5$ hydrocarbon liquid in a tank, a dimerization reaction can be included. During the injecting, the exothermic heat generated by the dimerization reaction can be quickly dissipated with low energy consumption, thereby reducing the operating costs. Furthermore, the $C_5$ hydrocarbon liquid in the tank can be used as the heat sink medium without need of extra cooling structures (e.g. cooling jacket and cooling coil), thereby reducing capital expenditure and operating costs.

Embodiments of the invention include a method of producing dicyclopentadiene ($C_{10}H_{12}$). The method includes flowing a $C_5$ hydrocarbon mixture stream that comprises cyclopentadiene ($C_5H_6$) to a tank. The method further includes injecting the $C_5$ hydrocarbon mixture stream as a jet stream into $C_5$ hydrocarbon liquid in the tank at a velocity in a range of 1 m/s to 10 m/s and under reaction conditions sufficient to dimerize the cyclopentadiene to form dicyclopentadiene.

Embodiments of the invention include a method of producing dicyclopentadiene ($C_{10}H_{12}$). The method includes flowing a $C_5$ hydrocarbon mixture stream that comprises cyclopentadiene ($C_5H_6$) to a tank. The method further includes injecting the $C_5$ hydrocarbon mixture stream as a jet stream into $C_5$ hydrocarbon liquid in the tank at a velocity in a range from 1 m/s to 10 m/s and under reaction conditions sufficient to dimerize the cyclopentadiene to form dicyclopentadiene. The injecting causes mixing of the $C_5$ hydrocarbon mixture stream and the $C_5$ hydrocarbon liquid.

Embodiments of the invention include a method of producing dicyclopentadiene ($C_{10}H_{12}$). The method includes flowing a $C_5$ hydrocarbon mixture stream that comprises cyclopentadiene ($C_5H_6$) to a tank. The method further includes injecting the $C_5$ hydrocarbon mixture stream as a jet stream into $C_5$ hydrocarbon liquid in the tank at a velocity in a range of 1 m/s to 10 m/s and under reaction conditions sufficient to dimerize the cyclopentadiene to form dicyclopentadiene. The reaction conditions include a reaction temperature of between 40° C. to 130° C. The injecting causes mixing of the $C_5$ hydrocarbon mixture stream and the $C_5$ hydrocarbon liquid.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %," "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "primarily," as that term is used in the specification and/or claims, means greater than any of 50 wt. %, 50 mol. %, or 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, include any measurable decrease or complete inhibition to achieve a desired result.

The term "effective," as that term is used in the specification and/or claims, means adequate to accomplish a desired, expected, or intended result.

The term "vertical angle," as that term is used in the specification and/or claims means an angle between a direction of injection and a horizontal plane.

The term "horizontal angle," as that term is used in the specification and/or claims means an angle, in a horizontal plane, between a direction of injection and a bisector of an angle that is formed by the left limit and right limit of the injection direction for the jet mixer.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

A method has been discovered for producing dicyclopentadiene from cyclopentadiene. The method uses a jet mixer in a reactor tank configured to inject $C_5$ hydrocarbon mixture comprising cyclopentadiene into a $C_5$ hydrocarbon liquid. The efficiency of mixing of the $C_5$ hydrocarbon mixture and the $C_5$ hydrocarbon liquid improves compared to mixing with an impeller. Furthermore, overheating of $C_5$ hydrocarbon mixture is avoided by using the jet mixer. Moreover, the jet mixer reduces large amounts of energy consumption for mixing the $C_5$ hydrocarbon mixture and the $C_5$ hydrocarbon liquid compared to mixing by an impeller, thereby reducing the operating costs.

Figure 1:
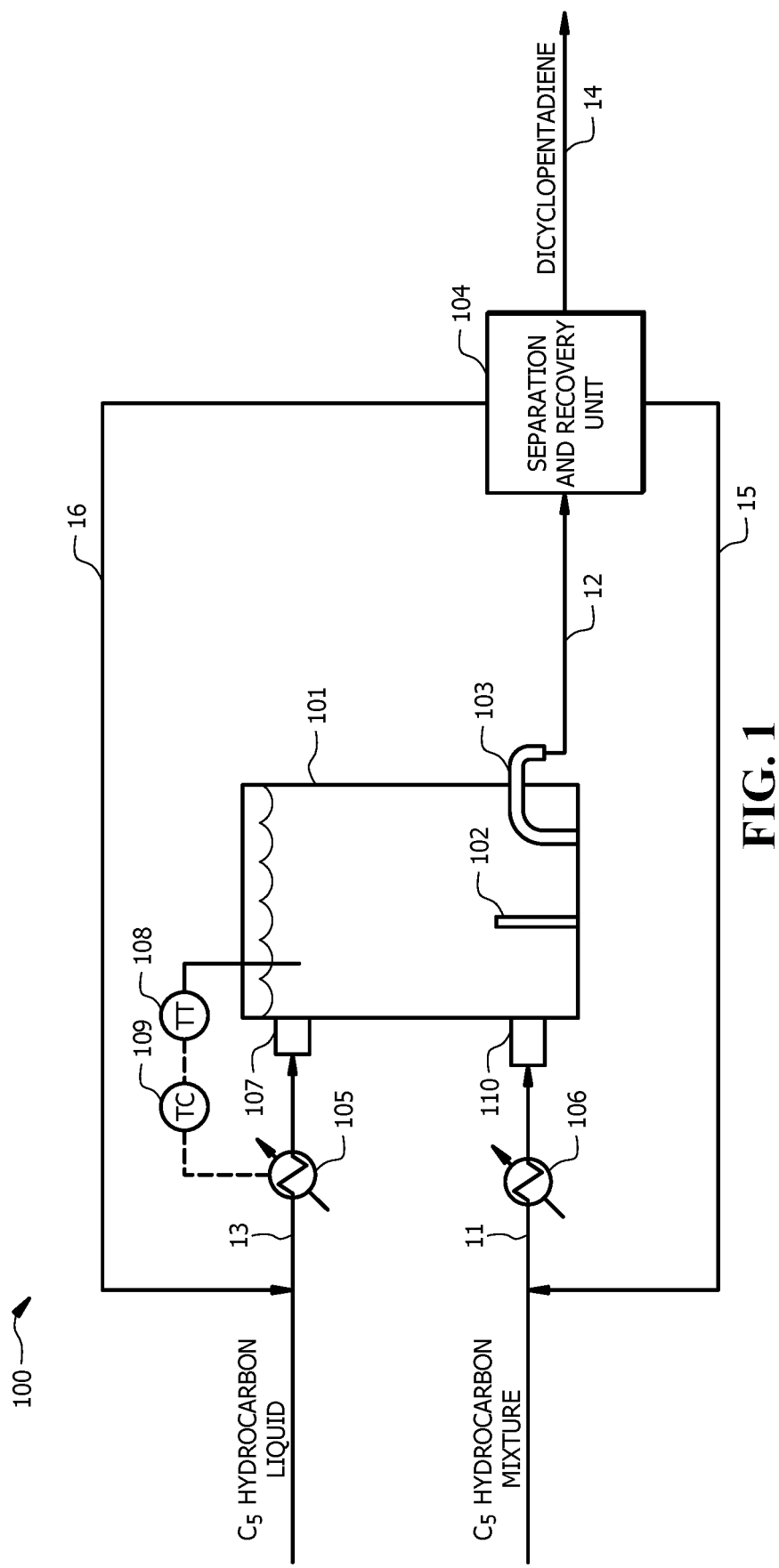
FIG. 1 shows a schematic diagram of a jet mixing system for producing dicyclopentadiene from cyclopentadiene via dimerization, according to embodiments of the invention.

With reference to FIG. 1, a schematic diagram is shown of jet mixing system 100 for dimerizing cyclopentadiene to form dicyclopentadiene, according to embodiments of the invention. Jet mixing system 100 may include reactor tank 101 as a container for holding liquid. In embodiments of the invention, the liquid is a $C_5$ hydrocarbon liquid. The $C_5$ hydrocarbon liquid may include $C_4$ linear hydrocarbons, $C_5$ linear hydrocarbons, $C_5$ cyclo hydrocarbons, $C_6$ linear hydrocarbons, $C_6$ cyclo hydrocarbons, or combinations thereof. In embodiments of the invention, reactor tank 101 may be in a shape that is substantially a horizontal cylinder, a vertical cylinder, a rectangle tank, a horizontal oval, a vertical oval, a horizontal capsule, or a vertical capsule. In embodiments of the invention, reactor tank 101 may be cylindrical or spherical.

According to embodiments of the invention, reactor tank 101 may include liquid inlet 107 adapted to receive the $C_5$ hydrocarbon liquid into reactor tank 101. In some instances, this flow of $C_5$ hydrocarbon liquid into the reactor tank may not be needed. In embodiments of the invention, jet mixing system 100 may further include first heat exchanger 105 in fluid communication with liquid inlet 107. According to embodiments of the invention, first heat exchanger 105 may be configured to heat or cool $C_5$ hydrocarbon liquid stream 13 such that $C_5$ hydrocarbon liquid stream 13 is in a temperature range of 40 to 130° C. and all ranges and values there between including ranges of 40 to 45° C., 45 to 50° C., 50 to 55° C., 55 to 60° C., 60 to 65° C., 65 to 70° C., 70 to 75° C., 75 to 80° C., 80 to 85° C., 85 to 90° C., 90 to 95° C., 95 to 100° C., 100 to 105° C., 105 to 110° C., 110 to 115° C., 115 to 120° C., 120 to 125° C., and 125 to 130° C. In embodiments of the invention, jet mixing system 100 may further include a temperature control system that comprises temperature transmitter 108 and temperature controller 109. Temperature transmitter 108 may be adapted to measure a temperature in reactor tank 101. Temperature controller may be adapted to adjust first heat exchanger 105 based on a temperature measurement from temperature transmitter 108 such that the temperature in reactor tank 101 is in a range of 40 to 130° C. and all ranges and values there between. When $C_5$ hydrocarbon liquid is not needed, the control system 108 and 109 can be connected to heat exchanger 106 instead.

Figure 2A:
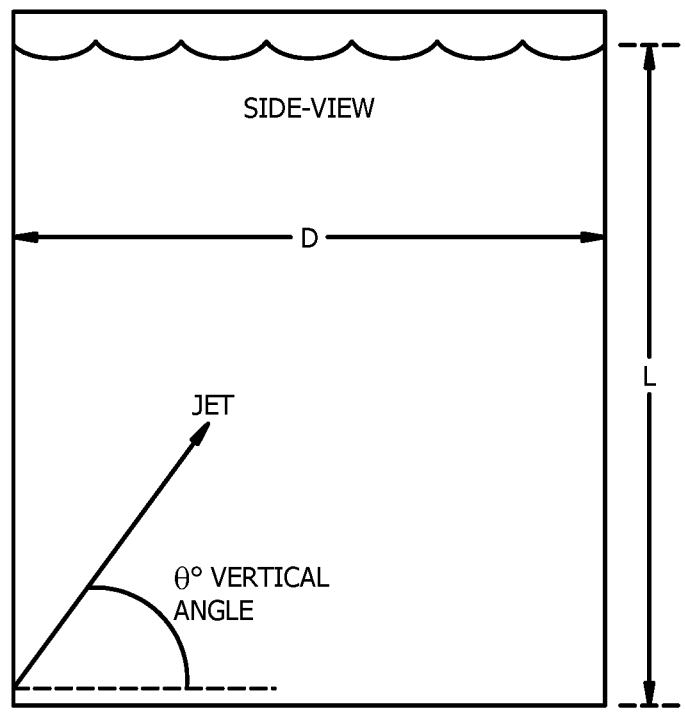
FIGS. 2A and 2B show a vertical angle and a horizontal angle of a jet stream in a jet mixing system for producing dicyclopentadiene from cyclopentadiene, according to embodiments of the invention.
Figure 2B:
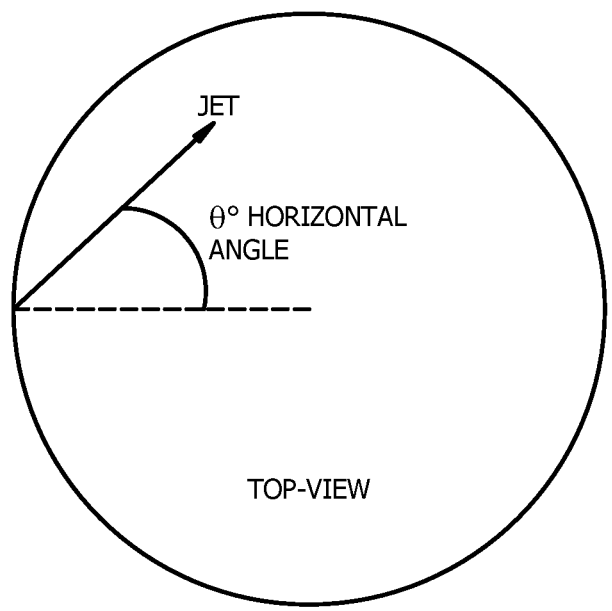

Jet mixing system 100 may further include jet inlet 102 disposed in tank 101. Jet inlet 102 may be adapted to inject a liquid to reactor tank 101. In embodiments of the invention, as shown in a side view of reactor tank 101 in FIG. 2A, jet inlet 102 may be adapted to inject a liquid at a vertical angle, which means an angle between a horizontal plane and a direction of injection, in a range of −75° to 75° and all ranges and values there between including ranges of −75° to −65°, −65° to −55°, −55° to −45°, −45° to −35°, −35° to −25°, −25° to −15°, −15° to −5°, −5° to −5°, 5° to 15°, 15° to 25°, 25° to 35°, 35° to 45°, 45° to 55°, 55° to 65°, and 65° to 75°. According to embodiments of the invention, as shown in a top view of reactor tank 101 in FIG. 2B, jet inlet 102 may be adapted to inject a liquid at a horizontal angle (θ in FIG. 2B) in a range of −75° to 75° and all ranges and values there between, including ranges of −75° to −65°, −65° to −55°, −55° to −45°, −45° to −35°, −35° to −25°, −25° to −15°, −15° to −5°, −5° to 5°, 5° to 15°, 15° to 25°, 25° to 35°, 35° to 45°, 45° to 55°, 55° to 65°, and 65° to 75°.

According to embodiments of the invention, jet inlet 102 may be adapted to inject a liquid at a velocity in a range of 1 m/s to 10 m/s and all ranges and values there between including 1 m/s, 2 m/s, 3 m/s, 4 m/s, 5 m/s, 6 m/s, 7 m/s, 8 m/s, 9 m/s, and 10 m/s. In embodiments of the invention, jet inlet 102 may be adapted to inject a liquid at a flow rate such that a residence time for a jet stream from jet inlet 102 is in a range of 3 to 30 hours and all ranges and values there between including 3 to 6 hours, 6 to 9 hours, 9 to 12 hours, 12 to 15 hours, 15 to 18 hours, 18 to 21 hours, 21 to 24 hours, 24 to 27 hours, and 27 to 30 hours. In embodiments of the invention, a flow rate of the jet stream from jet inlet 102 may be in a range of 10 to 100 $m^3 \cdot hr^{-1}$ and all ranges and values there between including 10 to 20 $m^3 \cdot hr^{-1}$, 20 to 30 $m^3 \cdot hr^{-1}$, 30 to 40 $m^3 \cdot hr^{-1}$, 40 to 50 $m^3 \cdot hr^{-1}$, 50 to 60 $m^3 \cdot hr^{-1}$, 60 to 70 $m^3 \cdot hr^{-1}$, 70 to 80 $m^3 \cdot hr^{-1}$, 80 to 90 $m^3 \cdot hr^{-1}$, and 90 to 100 $m^3 \cdot hr^{-1}$. A volume of the $C_5$ hydrocarbon liquid in reactor tank 101 may be in a range of 50 to 1000 $m^3$ and all ranges and values there between including 50 to 100 $m^3$, 100 to 150 $m^3$, 150 to 200 $m^3$, 200 to 250 $m^3$, 250 to 300 $m^3$, 300 to 350 $m^3$, 350 to 400 $m^3$, 400 to 450 $m^3$, 450 to 500 $m^3$, 500 to 550 $m^3$, 550 to 600 $m^3$, 600 to 650 $m^3$, 650 to 700 $m^3$, 700 to 750 $m^3$, 750 to 800 $m^3$, 800 to 850 $m^3$, 850 to 900 $m^3$, 900 to 950 $m^3$, and 950 to 1000 $m^3$. According to embodiments of the invention, the $C_5$ hydrocarbon liquid in reactor tank 101 may have a vertical height L and a diameter/width D such that a ratio of L to D is in a range of 0.5 to 1.5 and all ranges and values there between including 0.5, 0.6, 0.7, 0.8, 0.9, 1.0, 1.1, 1.2, 1.3, 1.4, and 1.5.

In embodiments of the invention, jet inlet 102 may be in fluid communication with feed inlet 110 configured to flow $C_5$ hydrocarbon mixture that comprises cyclopentadiene through jet inlet 102. In embodiments of the invention, jet mixing system 100 may further include second heat exchanger 106 adapted to heat and/or cool stream 11 of the $C_5$ hydrocarbon mixture flowing through jet inlet 102 such that a jet stream of $C_5$ hydrocarbon mixture injected from jet inlet 102 is at a temperature of 50 to 100° C. and all ranges and values there between, including ranges of 50 to 55° C., 55 to 60° C., 60 to 65° C., 65 to 70° C., 70 to 75° C., 75 to 80° C., 80 to 85° C., 85 to 90° C., 90 to 95° C., and 95 to 100° C.

In embodiments of the invention, jet mixing system 100 may include outlet 103, which leads from the inside to the outside of reactor tank 101. Outlet 103 may be adapted to flow effluent stream 12 from reactor tank 101. According to embodiments of the invention, jet mixing system 100 may be in fluid communication with separation and recovery unit 104. Separation and recovery unit 104 may be adapted to separate effluent stream 12 into product stream 14 that comprises primarily dicyclopentadiene, first recycle stream 15 that comprises unreacted cyclopentadiene, and second recycle stream 16 that comprises the $C_5$ hydrocarbon liquid. According to embodiments of the invention, first recycle stream 15 may be flowed into stream 11 of the $C_5$ hydrocarbon mixture. Second recycle stream 16 may be flowed into liquid stream 13 of the $C_5$ hydrocarbon liquid. If $C_5$ hydrocarbon liquid is not used, recycle stream 16 can be connected to $C_5$ hydrocarbon mixture.

Figure 3:
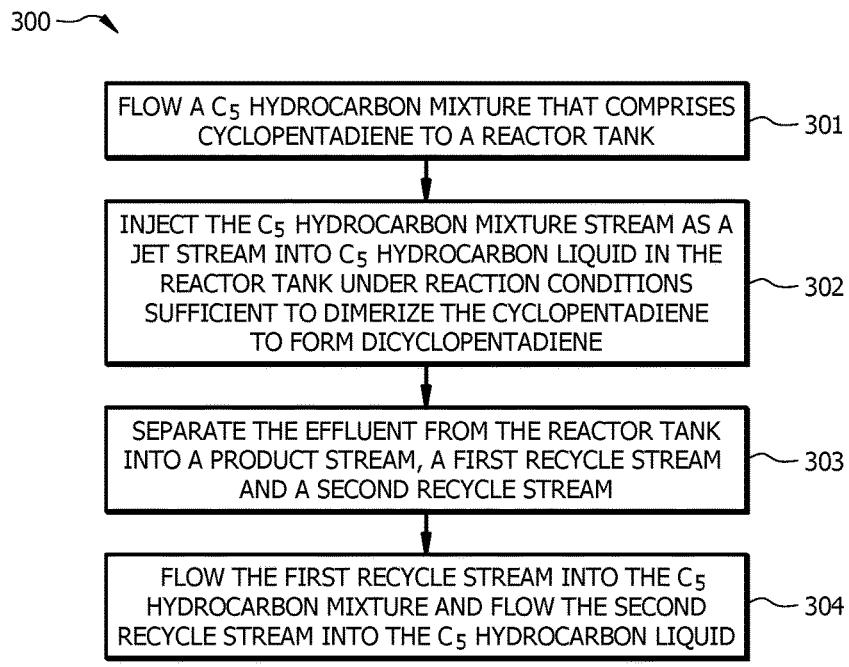
FIG. 3 shows a schematic flowchart for a method of producing dicyclopentadiene from cyclopentadiene, according to embodiments of the invention.

FIG. 3 shows method 300 for producing dicyclopentadiene from cyclopentadiene. Method 300 may be implemented by jet mixing system 100 as shown in FIG. 1. According to embodiments of the invention, method 300 may include flowing a $C_5$ hydrocarbon mixture stream (stream 11) that comprises cyclopentadiene ($C_5H_6$) to reactor tank 101, as shown in block 301. In embodiments of the invention, a typical composition of the $C_5$ hydrocarbon mixture stream may be 10 to 50 wt. % cyclopentadiene, 2 to 20 wt. % $C_4$ linear hydrocarbons, 30 to 80 wt. % $C_5$ linear and cyclo hydrocarbons and 0 to 10 wt. % $C_6$ linear and cyclo hydrocarbons. In embodiments of the invention, the $C_5$ hydrocarbon mixture may flow through second heat exchanger 106, then into reactor tank 101. The $C_5$ hydrocarbon mixture stream (stream 11) may be heated by second heat exchanger 106 to a temperature in a range of 50 to 100° C. and all ranges and values there between, including 50 to 52° C., 52 to 54° C., 54 to 56° C., 56 to 58° C., 58 to 60° C., 60 to 62° C., 62 to 64° C., 64 to 66° C., 66 to 68° C., 68 to 70° C., 70 to 72° C., 72 to 74° C., 74 to 76° C., 76 to 78° C., 78 to 80° C., 80 to 82° C., 82 to 84° C., 84 to 86° C., 86 to 88° C., 88 to 90° C., 90 to 92° C., 92 to 94° C., 94 to 96° C., 96 to 98° C., and 98 to 100° C.

In embodiments of the invention, method 300 may include injecting the $C_5$ hydrocarbon mixture stream as a jet stream into $C_5$ hydrocarbon liquid in reactor tank 101 under reaction conditions sufficient to dimerize the cyclopentadiene to form dicyclopentadiene, as shown in block 302. The jet stream may be injected at a velocity of 1 m/s to 10 m/s and all ranges and values there between including 1 m/s, 2 m/s, 3 m/s, 4 m/s, 5 m/s, 6 m/s, 7 m/s, 8 m/s, 9 m/s, and 10 m/s. As described above, the jet stream may be injected into reactor tank 101 at a vertical angle in a range of −75° to 75° and a horizontal angle in a range of −75° to 75°.

According to embodiments of the invention, the reaction conditions may include a reaction temperature of 40 to 130° C. and all ranges and values thereof including ranges of 40 to 45° C., 45 to 50° C., 50 to 55° C., 55 to 60° C., 60 to 65° C., 65 to 70° C., 70 to 75° C., 75 to 80° C., 80 to 85° C., 85 to 90° C., 90 to 95° C., 95 to 100° C., 100 to 105° C., 105 to 110° C., 110 to 115° C., 115 to 120° C., 120 to 125° C., and 125 to 130° C. Preferably, the reaction temperature may be in a range of 50 to 100° C. In embodiments of the invention, the jet stream from jet inlet 102 may have a temperature in a range of 40 to 80° C., and all ranges and values there between including 40 to 45° C., 45 to 50° C., 50 to 55° C., 55 to 60° C., 60 to 65° C., 65 to 70° C., 70 to 75° C., and 75 to 80° C. According to embodiments of the invention, the temperature of the $C_5$ hydrocarbon liquid may be at least 10 to 50° C. above the temperature of the jet stream. In embodiments of the invention, the jet stream may have a flowrate in a range of 10 to 100 $m^3 \cdot hr^{-1}$, and all ranges and values there between including 10 to 20 $m^3 \cdot hr^{-1}$ 20 to 30 $m^3 \cdot hr^{-1}$, 30 to 40 $m^3 \cdot hr^{-1}$, 40 to 50 $m^3 \cdot hr^{-1}$, 50 to 60 $m^3 \cdot hr^{-1}$, 60 to 70 $m^3 \cdot hr^{-1}$, 70 to 80 $m^3 \cdot hr^{-1}$, 80 to 90 $m^3 \cdot hr^{-1}$, and 90 to 100 $m^3 \cdot hr^{-1}$. $C_5$ hydrocarbon mixture may have a residence time in reactor tank 101 in a range of 180 to 1800 minutes and all ranges and values there between including 180 to 200 minutes, 200 to 300 minutes, 300 to 400 minutes, 400 to 500 minutes, 500 to 600 minutes, 600 to 700 minutes, 700 to 800 minutes, 800 to 900 minutes, 900 to 1000 minutes, 1000 to 1100 minutes, 1100 to 1200 minutes, 1200 to 1300 minutes, 1300 to 1400 minutes, 1400 to 1500 minutes, 1500 to 1600 minutes, 1600 to 1700 minutes, and 1700 to 1800 minutes. In embodiments of the invention, at blocks 301 and 302, jet mixing system 100 may be operated as a continuous system, a batch system, or a semi-batch system.

In embodiments of the invention, the injecting causes mixing of the $C_5$ hydrocarbon mixture stream from jet inlet 102 and the $C_5$ hydrocarbon liquid in reactor tank 101. The mixing process in the injecting may substantially follow a mixing process of an ideal continuous stirred-tank reactor. In embodiments of the invention, a mixing time for mixing the $C_5$ hydrocarbon mixture stream and the $C_5$ hydrocarbon liquid may be less than 600 minutes. According to embodiments of the invention, the $C_5$ hydrocarbon liquid in reactor tank 101 may be a heat sink liquid adapted to absorb heat generated by dimerizing cyclopentadiene. In embodiments of the invention, in the injecting step, substantially no $C_5$ hydrocarbon mixture or $C_5$ hydrocarbon liquid is overheated, thereby minimizing side reactions of polymerizing cyclopentadiene. The cyclopentadiene may have a conversion rate in a range of 70 to 90% and all ranges and values there between, including ranges of 70 to 72%, 72 to 74%, 74 to 76%, 76 to 78%, 78 to 80%, 80 to 82%, 82 to 84%, 84 to 86%, 86 to 88%, and 88 to 90%.

In embodiments of the invention, effluent stream 12 may be flowed to separation and recovery unit 104. According to embodiments of the invention, as shown at block 303, method 300 may further include separating effluent stream 12 into product stream 14 that comprises primarily dicyclopentadiene, first recycle stream 15 that comprises unreacted cyclopentadiene, and second recycle stream 16 that comprises the $C_5$ hydrocarbon liquid. In embodiments of the invention, as shown in block 304, method 300 may further include flowing first recycle stream 15 into stream 11 and flowing second recycle stream 16 into liquid stream 13 such that $C_5$ hydrocarbon liquid from effluent stream 12 and unreacted cyclopentadiene from effluent stream 12 can be recycled to reactor tank 101.

In summary, embodiments of the invention involve a method of producing dicyclopentadiene from cyclopentadiene. By using a jet mixer to inject a $C_5$ hydrocarbon mixture comprising cyclopentadiene into a $C_5$ hydrocarbon liquid, the energy consumption for the mixing process is significantly less than using conventional methods, thereby reducing operating costs of cyclopentadiene dimerization. Furthermore, the mixing by jet mixer can avoid the formation of any overheating spots in the $C_5$ hydrocarbon liquid and $C_5$ hydrocarbon mixture, thereby minimizing unwanted side reactions.

Although embodiments of the present invention have been described with reference to blocks of FIG. 3, it should be appreciated that operation of the present invention is not limited to the particular blocks and/or the particular order of the blocks illustrated in FIG. 3. Accordingly, embodiments of the invention may provide functionality as described herein using various blocks in a sequence different than that of FIG. 3.

As part of the disclosure of the present invention, specific examples are included below. The examples are for illustrative purposes only and are not intended to limit the invention. Those of ordinary skill in the art will readily recognize parameters that can be changed or modified to yield essentially the same results.

EXAMPLES

Example 1

Figure 4:
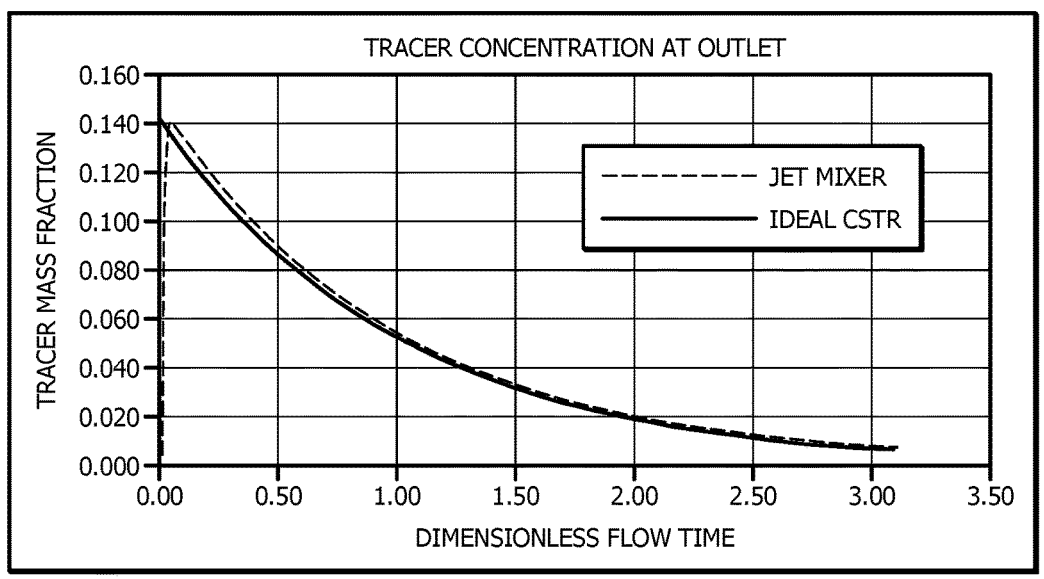
FIG. 4 shows simulation results of a correlation between tracer mass fraction at an outlet of a reactor tank and a dimensionless flow time in a process when a tracer is pulse injected into a reactor tank through a jet mixer.

Computational Fluid Dynamics Simulations on Liquid Mixing Process Using a Jet Mixer Computational Fluid Dynamics (CFD) simulations were run on liquid mixing process using a jet mixer in commercial CFD software ANSYS® FLUENT 17.2 platform. Tracer injections were simulated under a non-reacting isothermal condition. The tank size used for simulation was 300 m$^3$. The viscosity and density of the fluid was 0.2 cp and 700 kg/m$^3$, respectively. The tracer was pulse-injected through the jet mixer to the tank in all the simulations. As shown in FIG. 4, the simulation results indicate that the tracer concentration at the tank outlet substantially followed the mixing curve of an ideal continuous stirred-tank reactor (CSTR). Therefore, the jet mixer is highly efficient for mixing of liquid in a reactor tank. Furthermore, the mixing time in all the simulation runs was significantly shorter than the expected global residence time. In all the simulation runs, mixing time was calculated from the injection of the tracer until the time when the percentage deviation of the tracer concentration throughout the tank is less than 5% from the mean tracer concentration in the tank. Moreover, in all the simulation runs, the power consumption of the jet mixer was calculated. The results showed that the power for the jet mixer needed for mixing a liquid at a flowrate of 26.3 m$^3$/hr and jet stream velocity of 3.7 m/s in a 300000 liter tank was less than 1 horsepower, which is significantly lower than using impellers to mix the liquid at comparable efficiency.

Example 2

Figure 5:
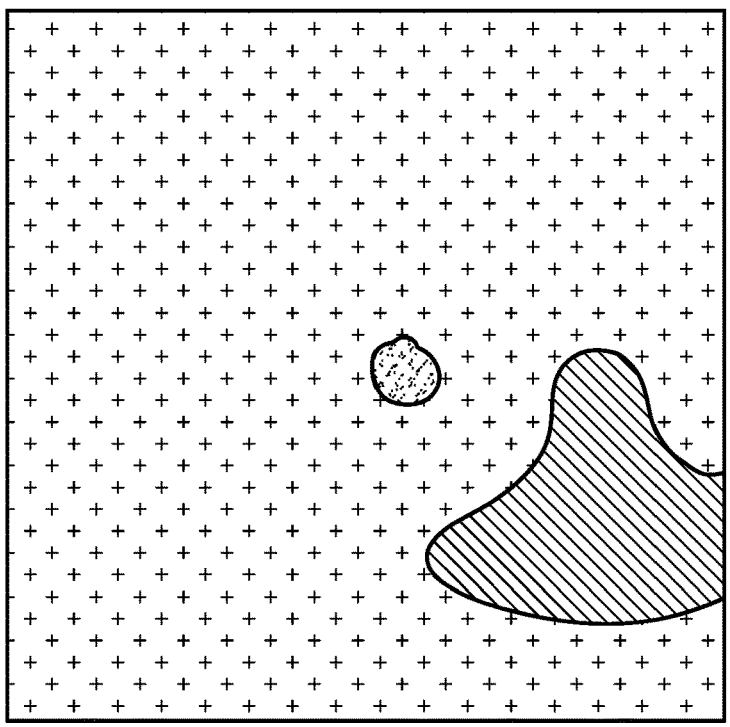
FIG. 5 shows dimensionless temperature contour in a reactor tank at two vertical planes from simulation runs of a method of producing dicyclopentadiene from cyclopentadiene, according to embodiments of the invention.
Figure 5:
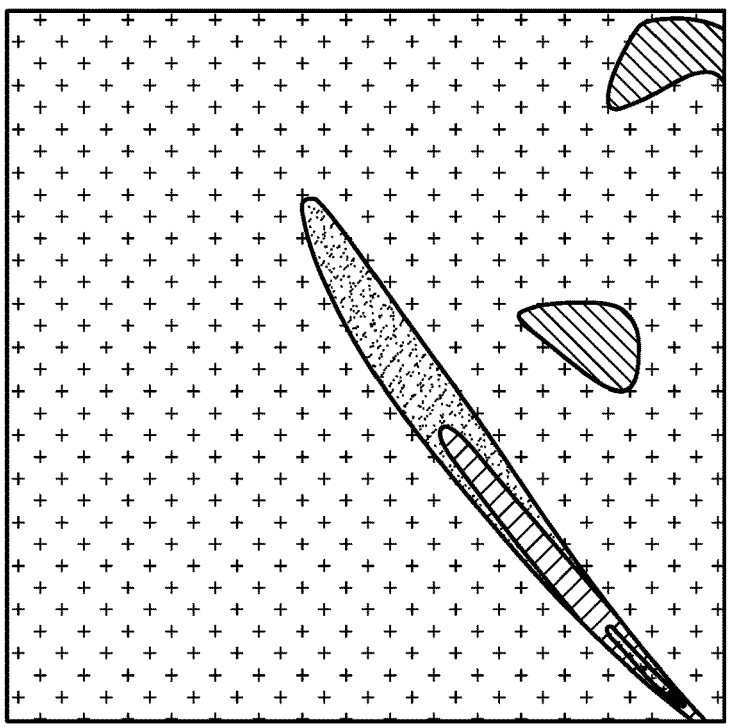
Figure 5:
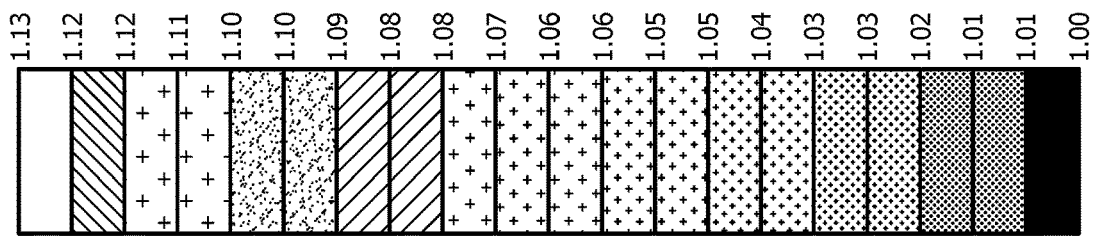

Computational Fluid Dynamic Simulations for Dimerization of Cyclopentadiene Using Jet Mixing Computational Fluid Dynamics (CFD) model was constructed in commercial CFD software ANSYS® FLUENT 17.2 platform. The reversible reaction of dimerizing cyclopentadiene to form dicyclopentadiene was included in the model. The reaction conditions for the simulation included a reaction temperature of 50° C., jet stream flowrate of 25 to 30 m$^3$/hr, jet stream velocity of 3 to 4 m/s, and a tank volume of 300 m$^3$. The simulation results showed that the temperature in the reactor tank was substantially uniform with deviation of temperature less than 5° C. from the mean temperature. The maximum temperature difference throughout the reactor tank is about 5° C. FIG. 5 shows dimensionless temperature contour in the reactor tank at two vertical planes, indicating substantially uniform temperature distribution in the reactor tank. In all simulation runs, no overheating spot (hot spot) was formed in the reactor tanks, thereby minimizing undesirable side reactions. The temperature throughout the reactor tank was within the limit to avoid undesirable reactions, which occur above 130° C. Furthermore, the simulation results show that the conversion rate of cyclopentadiene to dicyclopentadiene was more than 80%, which is significantly higher than the conversion rate of using conventional methods. Overall, the simulation results demonstrated that a jet mixing based method according to embodiments of the invention is superior to conventional methods that uses impellers for mixing the liquid in the reactor tank mainly due to short mixing time, avoidance of hot-spot formation, and high conversion rate.

In the context of the present invention, embodiments 1-17 are described. Embodiment 1 is a method of producing dicyclopentadiene ($C_{10}H_{12}$). The method includes flowing a $C_5$ hydrocarbon mixture stream that contains cyclopentadiene ($C_5H_6$) to a tank and injecting the $C_5$ hydrocarbon mixture stream as a jet stream into $C_5$ hydrocarbon liquid in the tank at a velocity in a range from 1 m/s to 10 m/s and under reaction conditions sufficient to dimerize the cyclopentadiene to form dicyclopentadiene. Embodiment 2 is the method of embodiment 1, wherein the injecting causes mixing of the $C_5$ hydrocarbon mixture stream and the $C_5$ hydrocarbon liquid. Embodiment 3 is the method of either of embodiments 1 and 2, wherein the reaction conditions include a jet stream temperature in a range of 40 to 130° C. Embodiment 4 is the method of embodiment 3, wherein the jet stream temperature is in a range of 50 to 100° C. Embodiment 5 is the method of any of embodiments 1 to 4, wherein the reaction conditions include a residence time of 180 to 1800 minutes. Embodiment 6 is the method of any of embodiments 1 to 5, wherein the jet stream is injected at a vertical angle in a range of −75 to +75 degrees. Embodiment 7 is the method of any of embodiments 1 to 6, wherein the jet stream is injected at a horizontal angle in a range of −75 degree to +75 degrees. Embodiment 8 is the method of any of embodiments 1 to 7, wherein the jet stream is injected in a tank having a liquid vertical height L and a diameter or width D such that a ratio of L to D is in a range of 0.5 to 1.5. Embodiment 9 is the method of any of embodiments 1 to 8, wherein the cyclopentadiene is converted to the dicyclopentadiene at a conversion rate in a range of 70 to 90%. Embodiment 10 is the method of any of embodiments 1 to 9, wherein the tank is substantially in a shape selected from the group consisting of horizontal cylinder, vertical cylinder, rectangle tank, horizontal oval, vertical oval, horizontal capsule, and vertical capsule. Embodiment 11 is the method of any of embodiments 1 to 9, wherein the tank is cylindrical or spherical. Embodiment 12 is the method of any of embodiments 1 to 11, wherein the jet stream has a flow rate of 10 to 100 $m^3 \cdot hr^{-1}$. Embodiment 13 is the method of any of embodiments 1 to 12, wherein the jet mixing has a mixing time of 180 to 1800 minutes. Embodiment 14 is the method of any of embodiments 1 to 13, wherein the $C_5$ hydrocarbon liquid in the tank has a volume of 50000 to 1000000 L to provide a heat sink for the dimerization reaction. Embodiment 15 is the method of any of embodiments 1 to 14, wherein the $C_5$ hydrocarbon liquid in the tank includes $C_5$ linear hydrocarbons, $C_5$ cyclo hydrocarbons or combinations thereof. Embodiment 16 is the method of any of embodiments 1 to 15, wherein the $C_5$ hydrocarbon mixture stream further includes $C_4$ linear hydrocarbons, $C_6$ linear hydrocarbons and $C_6$ cyclo hydrocarbons. Embodiment 17 is the method of any of embodiments 1 to 16, wherein the $C_5$ hydrocarbon liquid is at a temperature that is 10 to 50° C. above the jet stream temperature.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of producing dicyclopentadiene ($C_{10}H_{12}$), the method comprising:
    flowing a $C_5$ hydrocarbon mixture stream that comprises cyclopentadiene ($C_5H_6$) to a tank; and
    injecting the $C_5$ hydrocarbon mixture stream as a jet stream into a C5 hydrocarbon liquid in the tank at a velocity in a range from 1 m/s to 10 m/s and under reaction conditions sufficient to dimerize the cyclopentadiene to form dicyclopentadiene,
    wherein the injecting causes mixing of the $C_5$ hydrocarbon mixture stream and the $C_5$ hydrocarbon liquid,
    wherein the reaction conditions include a residence time of 180 to 1800 minutes, and
    wherein the jet stream is injected in a tank having a vertical height L and a diameter or width D such that a ratio of L to D is in a range of 0.5 to 1.5.

2. The method of claim 1, wherein the reaction conditions include a jet stream temperature in a range of 40 to 130° C.

3. The method of claim 2, wherein the jet stream temperature is in a range of 50 to 100° C.

4. The method of claim 1, wherein the jet stream is injected at a vertical angle in a range of −75 to +75 degrees.

5. The method of claim 1, wherein the jet stream is injected at a horizontal angle in a range of −75 degree to +75 degrees.

6. The method of claim 1, wherein the cyclopentadiene is converted to the dicyclopentadiene at a conversion rate in a range of 70 to 90%.

7. The method of claim 1, wherein the tank is substantially in a shape selected from the group consisting of horizontal cylinder, vertical cylinder, rectangle tank, horizontal oval, vertical oval, horizontal capsule, and vertical capsule.

8. The method of claim 1, wherein the tank is cylindrical or spherical.

9. The method of claim 1, wherein the jet stream has a flow rate of 10 to 100 $m^3 \cdot hr^{-1}$.

10. The method of claim 1, wherein the jet mixing has a mixing time of 180 to 1800 minutes.

11. The method of claim 1, wherein the $C_5$ hydrocarbon liquid in the tank has a volume of 50000 to 1000000 L to provide a heat sink for the dimerization reaction.

12. The method of claim 1, wherein the $C_5$ hydrocarbon liquid in the tank includes $C_5$ linear hydrocarbons, $C_5$ cyclo hydrocarbons or combinations thereof.

13. The method of claim 1, wherein the $C_5$ hydrocarbon mixture stream further comprises $C_4$ linear hydrocarbons, $C_6$ linear hydrocarbons and $C_6$ cyclo hydrocarbons.

14. The method of claim 1, wherein the $C_5$ hydrocarbon liquid is at a temperature that is 10 to 50° C. above the jet stream temperature.

15. The method of claim 1, wherein the $C_5$ hydrocarbon liquid in the tank includes $C_5$ linear hydrocarbons, $C_5$ cyclo hydrocarbons or combinations thereof.

16. The method of claim 1, wherein the $C_5$ hydrocarbon mixture stream further comprises $C_4$ linear hydrocarbons, $C_6$ linear hydrocarbons and $C_6$ cyclo hydrocarbons.

17. The method of claim 1, wherein the $C_5$ hydrocarbon liquid is at a temperature that is 10 to 50° C. above the jet stream temperature.

* * * * *